(12) United States Patent
Uyeda et al.

(10) Patent No.: US 6,294,184 B1
(45) Date of Patent: Sep. 25, 2001

(54) PROCESS FOR CONTROLLING LEPIDOPTERON PESTS

(75) Inventors: Kendrick Akira Uyeda; Gregory Alan Bradfisch, both of San Diego, CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 07/941,650

(22) Filed: Sep. 8, 1992

Related U.S. Application Data

(63) Continuation-in-part of application No. 07/758,020, filed on Sep. 12, 1991, now Pat. No. 5,286,485, which is a continuation-in-part of application No. 07/642,112, filed on Jan. 16, 1991, now Pat. No. 5,277,905, said application No. 07/758,020, is a continuation-in-part of application No. 07/658,935, filed on Feb. 21, 1991, now abandoned.

(51) Int. Cl.[7] ............................. A01N 25/00; C12N 1/00; C12N 15/74; C07H 21/04
(52) U.S. Cl. .......................... 424/405; 435/243; 435/471; 536/23.1
(58) Field of Search ................................ 435/69.1, 252.3, 435/252.31, 252.33, 252.34, 254.11, 243, 471; 424/93.461, 405; 536/23.1

(56) References Cited

U.S. PATENT DOCUMENTS

| | | | | |
|---|---|---|---|---|
| 4,849,217 | * | 7/1989 | Soares | 424/93.461 |
| 4,996,155 | * | 2/1991 | Sick | 455/93.2 |
| 5,126,133 | * | 6/1992 | Payne | 424/93.461 |

* cited by examiner

*Primary Examiner*—Terry McKelvey
*Assistant Examiner*—William Sandals
(74) *Attorney, Agent, or Firm*—Saliwanchik, Lloyd & Saliwanchik

(57) ABSTRACT

The subject disclosure concerns *Bacillus thuringiensis* strains which can be used to control lepidopteran pests. The strains were previously known to control coleopteran pests. The discovery of lepidopteran activity was totally unexpected. These B.t. strains can be formulated using standard lepidopteran formulation procedures. Means of administration are also standard. The genes encoding lepidopteran-active toxins can be isolated from the B.t. isolates and used to transform other microbes or plants for use to control lepidopteran pests.

20 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 3471 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Bacillus thuringiensis
       (B) STRAIN: kumamotoensis
       (C) INDIVIDUAL ISOLATE: PS50C (vii) IMMEDIATE SOURCE:
       (B) CLONE: E. coli NM522(pMYC1638), NRRL B-18751

(xi) SEQUENCE DESCRIPTION: SEQ ID NO:1:

```
ATGAGTCCAA ATAATCAAAA TGAATATGAA ATTATAGATG CGACACCTTC TACATCTGTA      60
TCCAGTGATT CTAACAGATA CCCTTTTGCG AATGAGCCAA CAGATGCGTT ACAAAATATG     120
AATTATAAAG ATTATCTGAA AATGTCTGGG GGAGAGAATC CTGAATTATT TGGAAATCCG     180
GAGACGTTTA TTAGTTCATC CACGATTCAA ACTGGAATTG GCATTGTTGG TCGAATACTA     240
GGAGCTTTAG GGTTCCATT TGCTAGTCAG ATAGCTAGTT TCTATAGTTT CATTGTTGGT     300
CAATTATGGC CGTCAAAGAG CGTAGATATA TGGGGAGAAA TTATGGAACG AGTGGAAGAA     360
CTCGTTGATC AAAAAATAGA AAAATATGTA AAAGATAAGG CTCTTGCTGA ATTAAAAGGG     420
CTAGGAAATG CTTTGGATGT ATATCAGCAG TCACTTGAAG ATTGGCTGGA AAATCGCAAT     480
GATGCAAGAA CTAGAAGTGT TGTTTCTAAT CAATTTATAG CTTTAGATCT TAACTTTGTT     540
AGTTCAATTC CATCTTTTGC AGTATCCGGA CACGAAGTAC TATTATTAGC AGTATATGCA     600
CAGGCTGTGA ACCTACATTT ATTGTTATTA AGAGATGCTT CTATTTTTGG AGAAGAGTGG     660
GGATTTACAC CAGGTGAAAT TTCTAGATTT TATAATCGTC AAGTGCAACT TACCGCTGAA     720
TATTCAGACT ATTGTGTAAA GTGGTATAAA ATCGGCTTAG ATAAATTGAA AGGTACCACT     780
TCTAAAAGTT GGCTGAATTA TCATCAGTTC CGTAGAGAGA TGACATTACT GGTATTAGAT     840
TTGGTGGCGT TATTTCCAAA CTATGACACA CATATGTATC CAATCGAAAC AACAGCTCAA     900
CTTACACGGG ATGTGTATAC AGATCCGATA GCATTTAACA TAGTGACAAG TACTGGATTC     960
TGCAACCCTT GGTCAACCCA CAGTGGTATT CTTTTTTATG AAGTTGAAAA CAACGTAATT    1020
CGTCCGCCAC ACTTGTTTGA TATACTCAGC TCAGTAGAAA TTAATACAAG TAGAGGGGGT    1080
ATTACGTTAA ATAATGATGC ATATATAAAC TACTGGTCAG GACATACCCT AAAATATCGT    1140
AGAACAGCTG ATTCGACCGT AACATACACA GCTAATTACG GTCGAATCAC TTCAGAAAAG    1200
AATTCATTTG CACTTGAGGA TAGGGATATT TTTGAAATTA ATTCAACTGT GGCAAACCTA    1260
GCTAATTACT ACCAAAAGGC ATATGGTGTG CCGGGATCTT GGTTCCATAT GGTAAAAAGG    1320
GGAACCTCAT CAACAACAGC GTATTTATAT TCAAAAACAC ATACAGCTCT CCAAGGGTGT    1380
ACACAGGTTT ATGAATCAAG TGATGAAATA CCTCTAGATA GAACTGTACC GGTAGCTGAA    1440
```

```
AGCTATAGTC ATAGATTATC TCATATTACC TCCCATTCTT TCTCTAAAAA TGGGAGTGCA    1500

TACTATGGGA GTTTCCCTGT ATTTGTTTGG ACACATACTA GTGCGGATTT AAATAATACA    1560

ATATATTCAG ATAAAATCAC TCAAATTCCA GCGGTAAAGG GAGACATGTT ATATCTAGGG    1620

GGTTCCGTAG TACAGGGTCC TGGATTTACA GGAGGAGATA TATTAAAAAG AACCAATCCT    1680

AGCATATTAG GGACCTTTGC GGTTACAGTA AATGGGTCGT TATCACAAAG ATATCGTGTA    1740

AGAATTCGCT ATGCCTCTAC AACAGATTTT GAATTTACTC TATACCTTGG CGACACAATA    1800

GAAAAAAATA GATTTAACAA AACTATGGAT AATGGGGCAT CTTTAACGTA TGAAACATTT    1860

AAATTCGCAA GTTTCATTAC TGATTTCCAA TTCAGAGAAA CACAAGATAA AATACTCCTA    1920

TCCATGGGTG ATTTTAGCTC CGGTCAAGAA GTTTATATAG ACCGAATCGA ATTCATCCCA    1980

GTAGATGAGA CATATGAGGC GGAACAAGAT TTAGAAGCGG CGAAGAAAGC AGTGAATGCC    2040

TTGTTTACGA ATACAAAAGA TGGCTTACGA CCAGGTGTAA CGGATTATGA AGTAAATCAA    2100

GCGGCAAACT TAGTGGAATG CCTATCGGAT GATTTATATC CAAATGAAAA ACGATTGTTA    2160

TTTGATGCGG TGAGAGAGGC AAAACGCCTC AGTGGGCAC GTAACTTACT ACAAGATCCA     2220

GATTTCCAAG AGATAAACGG AGAAAATGGA TGGGCGGCAA GTACGGGAAT TGAGATTGTA    2280

GAAGGGGATG CTGTATTTAA AGGACGTTAT CTACGCCTAC CAGGTGCACG AGAAATTGAT    2340

ACGGAAACGT ATCCAACGTA TCTGTATCAA AAAGTAGAGG AAGGTGTATT AAAACCATAC    2400

ACAAGATATA GACTGAGAGG GTTTGTGGGA AGTAGTCAAG GATTAGAAAT TTATACGATA    2460

CGTCACCAAA CGAATCGAAT TGTAAAGAAT GTACCAGATG ATTTATTGCC AGATGTATCT    2520

CCTGTAAACT CTGATGGCAG TATCAATCGA TGCAGCGAAC AAAAGTATGT GAATAGCCGT    2580

TTAGAAGGAG AAAACCGTTC TGGTGATGCA CATGAGTTCT CGCTCCCTAT CGATATAGGA    2640

GAGCTGGATT ACAATGAAAA TGCAGGAATA TGGGTTGGAT TTAAGATTAC GGACCCAGAG    2700

GGATACGCAA CACTTGGAAA TCTTGAATTA GTCGAAGAGG GACCTTTGTC AGGAGACGCA    2760

TTAGAGCGCT TGCAAAGAGA AGAACAACAG TGGAAGATTC AAATGACAAG AAGACGTGAA    2820

GAGACAGATA GAAGATACAT GGCATCGAAA CAAGCGGTAG ATCGTTTATA TGCCGATTAT    2880

CAGGATCAAC AACTGAATCC TGATGTAGAG ATTACAGATC TTACTGCGGC TCAAGATCTG    2940

ATACAGTCCA TTCCTTACGT ATATAACGAA ATGTTCCCAG AAATACCAGG GATGAACTAT    3000

ACGAAGTTTA CAGAATTAAC AGATCGACTC CAACAAGCGT GGAATTTGTA TGATCAGCGA    3060

AATGCCATAC CAAATGGTGA TTTTCGAAAT GGGTTAAGTA ATTGGAATGC AACGCCTGGC    3120

GTAGAAGTAC AACAAATCAA TCATACATCT GTCCTTGTGA TTCCAAACTG GGATGAACAA    3180

GTTTCACAAC AGTTTACAGT TCAACCGAAT CAAAGATATG TATTACGAGT TACTGCAAGA    3240

AAAGAAGGGG TAGGAAATGG ATATGTAAGT ATTCGTGATG GTGGAAATCA ATCAGAAACG    3300

CTTACTTTTA GTGCAAGCGA TTATGATACA AATGGTGTGT ATAATGACCA AACCGGCTAT    3360

ATCACAAAAA CAGTGACATT CATCCCGTAT ACAGATCAAA TGTGGATTGA AATAAGTGAA    3420

ACAGAAGGTA CGTTCTATAT AGAAAGTGTA GAATTGATTG TAGACGTAGA G             3471
```

(2) INFORMATION FOR SEQ ID NO:2:

(i) SEQUENCE CHARACTERISTICS:
        (A) LENGTH: 1157 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
    (A) ORGANISM: Bacillus thuringiensis
    (B) STRAIN: kumamotoensis
    (C) INDIVIDUAL ISOLATE: PS50C (vii) IMMEDIATE SOURCE:
    (B) CLONE: E. coli NM522(pMYC1638), NRRL B-18751

(xi) SEQUENCE DESCRIPTION: SEQ ID NO:2:

```
Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
                20                  25                  30

Pro Thr Asp Ala Leu Gln Asn Met Asn Tyr Lys Asp Tyr Leu Lys Met
            35                  40                  45

Ser Gly Gly Glu Asn Pro Glu Leu Phe Gly Asn Pro Glu Thr Phe Ile
        50                  55                  60

Ser Ser Ser Thr Ile Gln Thr Gly Ile Gly Ile Val Gly Arg Ile Leu
65                  70                  75                  80

Gly Ala Leu Gly Val Pro Phe Ala Ser Gln Ile Ala Ser Phe Tyr Ser
                85                  90                  95

Phe Ile Val Gly Gln Leu Trp Pro Ser Lys Ser Val Asp Ile Trp Gly
                100                 105                 110

Glu Ile Met Glu Arg Val Glu Glu Leu Val Asp Gln Lys Ile Glu Lys
            115                 120                 125

Tyr Val Lys Asp Lys Ala Leu Ala Glu Leu Lys Gly Leu Gly Asn Ala
        130                 135                 140

Leu Asp Val Tyr Gln Gln Ser Leu Glu Asp Trp Leu Glu Asn Arg Asn
145                 150                 155                 160

Asp Ala Arg Thr Arg Ser Val Val Ser Asn Gln Phe Ile Ala Leu Asp
                165                 170                 175

Leu Asn Phe Val Ser Ser Ile Pro Ser Phe Ala Val Ser Gly His Glu
                180                 185                 190

Val Leu Leu Leu Ala Val Tyr Ala Gln Ala Val Asn Leu His Leu Leu
            195                 200                 205

Leu Leu Arg Asp Ala Ser Ile Phe Gly Glu Glu Trp Gly Phe Thr Pro
        210                 215                 220

Gly Glu Ile Ser Arg Phe Tyr Asn Arg Gln Val Gln Leu Thr Ala Glu
225                 230                 235                 240

Tyr Ser Asp Tyr Cys Val Lys Trp Tyr Lys Ile Gly Leu Asp Lys Leu
                245                 250                 255

Lys Gly Thr Thr Ser Lys Ser Trp Leu Asn Tyr His Gln Phe Arg Arg
            260                 265                 270

Glu Met Thr Leu Leu Val Leu Asp Leu Val Ala Leu Phe Pro Asn Tyr
        275                 280                 285

Asp Thr His Met Tyr Pro Ile Glu Thr Thr Ala Gln Leu Thr Arg Asp
        290                 295                 300

Val Tyr Thr Asp Pro Ile Ala Phe Asn Ile Val Thr Ser Thr Gly Phe
305                 310                 315                 320

Cys Asn Pro Trp Ser Thr His Ser Gly Ile Leu Phe Tyr Glu Val Glu
                325                 330                 335

Asn Asn Val Ile Arg Pro Pro His Leu Phe Asp Ile Leu Ser Ser Val
```

-continued

```
                    340                 345                 350
Glu Ile Asn Thr Ser Arg Gly Gly Ile Thr Leu Asn Asn Asp Ala Tyr
            355                 360                 365
Ile Asn Tyr Trp Ser Gly His Thr Leu Lys Tyr Arg Arg Thr Ala Asp
        370                 375                 380
Ser Thr Val Thr Tyr Thr Ala Asn Tyr Gly Arg Ile Thr Ser Glu Lys
385                 390                 395                 400
Asn Ser Phe Ala Leu Glu Asp Arg Asp Ile Phe Glu Ile Asn Ser Thr
                405                 410                 415
Val Ala Asn Leu Ala Asn Tyr Tyr Gln Lys Ala Tyr Gly Val Pro Gly
            420                 425                 430
Ser Trp Phe His Met Val Lys Arg Gly Thr Ser Thr Thr Ala Tyr
        435                 440                 445
Leu Tyr Ser Lys Thr His Thr Ala Leu Gln Gly Cys Thr Gln Val Tyr
    450                 455                 460
Glu Ser Ser Asp Glu Ile Pro Leu Asp Arg Thr Val Pro Val Ala Glu
465                 470                 475                 480
Ser Tyr Ser His Arg Leu Ser His Ile Thr Ser His Ser Phe Ser Lys
                485                 490                 495
Asn Gly Ser Ala Tyr Tyr Gly Ser Phe Pro Val Phe Trp Thr His
            500                 505                 510
Thr Ser Ala Asp Leu Asn Asn Thr Ile Tyr Ser Asp Lys Ile Thr Gln
        515                 520                 525
Ile Pro Ala Val Lys Gly Asp Met Leu Tyr Leu Gly Gly Ser Val Val
    530                 535                 540
Gln Gly Pro Gly Phe Thr Gly Gly Asp Ile Leu Lys Arg Thr Asn Pro
545                 550                 555                 560
Ser Ile Leu Gly Thr Phe Ala Val Thr Val Asn Gly Ser Leu Ser Gln
                565                 570                 575
Arg Tyr Arg Val Arg Ile Arg Tyr Ala Ser Thr Thr Asp Phe Glu Phe
            580                 585                 590
Thr Leu Tyr Leu Gly Asp Thr Ile Glu Lys Asn Arg Phe Asn Lys Thr
        595                 600                 605
Met Asp Asn Gly Ala Ser Leu Thr Tyr Glu Thr Phe Lys Phe Ala Ser
    610                 615                 620
Phe Ile Thr Asp Phe Gln Phe Arg Glu Thr Gln Asp Lys Ile Leu Leu
625                 630                 635                 640
Ser Met Gly Asp Phe Ser Ser Gly Gln Glu Val Tyr Ile Asp Arg Ile
                645                 650                 655
Glu Phe Ile Pro Val Asp Glu Thr Tyr Glu Ala Glu Gln Asp Leu Glu
            660                 665                 670
Ala Ala Lys Lys Ala Val Asn Ala Leu Phe Thr Asn Thr Lys Asp Gly
        675                 680                 685
Leu Arg Pro Gly Val Thr Asp Tyr Glu Val Asn Gln Ala Ala Asn Leu
    690                 695                 700
Val Glu Cys Leu Ser Asp Leu Tyr Pro Asn Glu Lys Arg Leu Leu
705                 710                 715                 720
Phe Asp Ala Val Arg Glu Ala Lys Arg Leu Ser Gly Ala Arg Asn Leu
                725                 730                 735
Leu Gln Asp Pro Asp Phe Gln Glu Ile Asn Gly Glu Asn Gly Trp Ala
            740                 745                 750
Ala Ser Thr Gly Ile Glu Ile Val Glu Gly Asp Ala Val Phe Lys Gly
        755                 760                 765
```

-continued

```
Arg Tyr Leu Arg Leu Pro Gly Ala Arg Glu Ile Asp Thr Glu Thr Tyr
    770                 775                 780
Pro Thr Tyr Leu Tyr Gln Lys Val Glu Glu Gly Val Leu Lys Pro Tyr
785                 790                 795                 800
Thr Arg Tyr Arg Leu Arg Gly Phe Val Gly Ser Ser Gln Gly Leu Glu
            805                 810                 815
Ile Tyr Thr Ile Arg His Gln Thr Asn Arg Ile Val Lys Asn Val Pro
                820                 825                 830
Asp Asp Leu Leu Pro Asp Val Ser Pro Val Asn Ser Asp Gly Ser Ile
            835                 840                 845
Asn Arg Cys Ser Glu Gln Lys Tyr Val Asn Ser Arg Leu Glu Gly Glu
850                 855                 860
Asn Arg Ser Gly Asp Ala His Glu Phe Ser Leu Pro Ile Asp Ile Gly
865                 870                 875                 880
Glu Leu Asp Tyr Asn Glu Asn Ala Gly Ile Trp Val Gly Phe Lys Ile
                885                 890                 895
Thr Asp Pro Glu Gly Tyr Ala Thr Leu Gly Asn Leu Glu Leu Val Glu
            900                 905                 910
Glu Gly Pro Leu Ser Gly Asp Ala Leu Glu Arg Leu Gln Arg Glu Glu
        915                 920                 925
Gln Gln Trp Lys Ile Gln Met Thr Arg Arg Glu Glu Thr Asp Arg
930                 935                 940
Arg Tyr Met Ala Ser Lys Gln Ala Val Asp Arg Leu Tyr Ala Asp Tyr
945                 950                 955                 960
Gln Asp Gln Gln Leu Asn Pro Asp Val Glu Ile Thr Asp Leu Thr Ala
            965                 970                 975
Ala Gln Asp Leu Ile Gln Ser Ile Pro Tyr Val Tyr Asn Glu Met Phe
        980                 985                 990
Pro Glu Ile Pro Gly Met Asn Tyr Thr Lys Phe Thr Glu Leu Thr Asp
            995                 1000                1005
Arg Leu Gln Gln Ala Trp Asn Leu Tyr Asp Gln Arg Asn Ala Ile Pro
    1010                1015                1020
Asn Gly Asp Phe Arg Asn Gly Leu Ser Asn Trp Asn Ala Thr Pro Gly
1025                1030                1035                1040
Val Glu Val Gln Gln Ile Asn His Thr Ser Val Leu Val Ile Pro Asn
                1045                1050                1055
Trp Asp Glu Gln Val Ser Gln Gln Phe Thr Val Gln Pro Asn Gln Arg
            1060                1065                1070
Tyr Val Leu Arg Val Thr Ala Arg Lys Glu Gly Val Gly Asn Gly Tyr
        1075                1080                1085
Val Ser Ile Arg Asp Gly Gly Asn Gln Ser Glu Thr Leu Thr Phe Ser
    1090                1095                1100
Ala Ser Asp Tyr Asp Thr Asn Gly Val Tyr Asn Asp Gln Thr Gly Tyr
1105                1110                1115                1120
Ile Thr Lys Thr Val Thr Phe Ile Pro Tyr Thr Asp Gln Met Trp Ile
                1125                1130                1135
Glu Ile Ser Glu Thr Glu Gly Thr Phe Tyr Ile Glu Ser Val Glu Leu
            1140                1145                1150
Ile Val Asp Val Glu
            1155
```

(2) INFORMATION FOR SEQ ID NO:3:

(i) SEQUENCE CHARACTERISTICS:
       (A) LENGTH: 1953 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Bacillus thuringiensis
       (B) STRAIN: tolworthi
       (C) INDIVIDUAL ISOLATE: 43f (vii) IMMEDIATE SOURCE:
       (B) CLONE: E. coli XL1-Blue (pM1,98-4), NRRL B-18291

(ix) FEATURE:
       (A) NAME/KEY: CDS
       (B) LOCATION: 1..1953

(xi) SEQUENCE DESCRIPTION: SEQ ID NO:3:

```
ATG AAT CCA AAC AAT CGA AGT GAA TAT GAT ACG ATA AAG GTT ACA CCT      48
Met Asn Pro Asn Asn Arg Ser Glu Tyr Asp Thr Ile Lys Val Thr Pro
 1               5                  10                  15

AAC AGT GAA TTG CCA ACT AAC CAT AAT CAA TAT CCT TTA GCT GAC AAT      96
Asn Ser Glu Leu Pro Thr Asn His Asn Gln Tyr Pro Leu Ala Asp Asn
            20                  25                  30

CCA AAT TCG ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
        35                  40                  45

ACT GCA GAC AAT TCT ACG GAA GTG CTA GAC AGC TCT ACA GTA AAA GAT     192
Thr Ala Asp Asn Ser Thr Glu Val Leu Asp Ser Ser Thr Val Lys Asp
    50                  55                  60

GCA GTT GGG ACA GGA ATT TCT GTT GTA GGA CAG ATT TTA GGT GTT GTA     240
Ala Val Gly Thr Gly Ile Ser Val Val Gly Gln Ile Leu Gly Val Val
65                  70                  75                  80

GGG GTT CCA TTT GCT GGG GCG CTC ACT TCA TTT TAT CAA TCA TTT CTT     288
Gly Val Pro Phe Ala Gly Ala Leu Thr Ser Phe Tyr Gln Ser Phe Leu
                85                  90                  95

AAC GCT ATA TGG CCA AGT GAT GCT GAC CCA TGG AAG GCT TTT ATG GCA     336
Asn Ala Ile Trp Pro Ser Asp Ala Asp Pro Trp Lys Ala Phe Met Ala
            100                 105                 110

CAA GTG GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTT GAA GAT TAT     432
Lys Ala Leu Ala Glu Leu Gln Gly Leu Gln Asn Asn Phe Glu Asp Tyr
    130                 135                 140

GTA AAT GCG TTG GAT TCC TGG AAG AAA GCG CCT GTA AAT TTA CGA AGT     480
Val Asn Ala Leu Asp Ser Trp Lys Lys Ala Pro Val Asn Leu Arg Ser
145                 150                 155                 160

CGA AGA AGC CAA GAT CGA ATA AGA GAA CTT TTT TCT CAA GCA GAA AGC     528
Arg Arg Ser Gln Asp Arg Ile Arg Glu Leu Phe Ser Gln Ala Glu Ser
                165                 170                 175

CAT TTT CGT AAT TCC ATG CCG TCA TTT GCG GTT TCC AAA TTC GAA GTT     576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA     624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA     672
```

```
Leu Lys Asp Ala Gln Val Phe Gly Glu Glu Trp Gly Tyr Ser Ser Glu
    210                 215                 220

GAT ATT GCT GAA TTT TAT CAA AGA CAA TTA AAA CTT ACG CAA CAA TAC        720
Asp Ile Ala Glu Phe Tyr Gln Arg Gln Leu Lys Leu Thr Gln Gln Tyr
225                 230                 235                 240

ACT GAC CAT TGT GTC AAT TGG TAT AAT GTT GGA TTA AAT AGT TTA AGA        768
Thr Asp His Cys Val Asn Trp Tyr Asn Val Gly Leu Asn Ser Leu Arg
                245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
            260                 265                 270

ATG ACA TTA ACT GTA TTA GAT CTA ATT GTA TTA TTC CCA TTT TAT GAT        864
Met Thr Leu Thr Val Leu Asp Leu Ile Val Leu Phe Pro Phe Tyr Asp
        275                 280                 285

GTT CGG TTA TAC TCA AAA GGA GTT AAA ACA GAA CTA ACA AGA GAC ATT        912
Val Arg Leu Tyr Ser Lys Gly Val Lys Thr Glu Leu Thr Arg Asp Ile
    290                 295                 300

TTT ACA GAT CCA ATT TTT ACA CTC AAT GCT CTT CAA GAG TAT GGA CCA        960
Phe Thr Asp Pro Ile Phe Thr Leu Asn Ala Leu Gln Glu Tyr Gly Pro
305                 310                 315                 320

ACT TTT TCG AGT ATA GAA AAC TCT ATT CGA AAA CCT CAT TTA TTT GAT       1008
Thr Phe Ser Ser Ile Glu Asn Ser Ile Arg Lys Pro His Leu Phe Asp
                325                 330                 335

TAT TTG CGT GGG ATT GAA TTT CAT ACG CGT CTT CGA CCT GGT TAC TCT       1056
Tyr Leu Arg Gly Ile Glu Phe His Thr Arg Leu Arg Pro Gly Tyr Ser
            340                 345                 350

GGG AAA GAT TCT TTC AAT TAT TGG TCT GGT AAT TAT GTA GAA ACT AGA       1104
Gly Lys Asp Ser Phe Asn Tyr Trp Ser Gly Asn Tyr Val Glu Thr Arg
        355                 360                 365

CCT AGT ATA GGA TCT AAT GAT ACA ATC ACT TCC CCA TTT TAT GGA GAT       1152
Pro Ser Ile Gly Ser Asn Asp Thr Ile Thr Ser Pro Phe Tyr Gly Asp
    370                 375                 380

AAA TCT ATT GAA CCT ATA CAA AAG CTA AGC TTT GAT GGA CAA AAA GTT       1200
Lys Ser Ile Glu Pro Ile Gln Lys Leu Ser Phe Asp Gly Gln Lys Val
385                 390                 395                 400

TAT CGA ACT ATA GCT AAT ACA GAC ATA GCG GCT TTT CCG GAT GGC AAG       1248
Tyr Arg Thr Ile Ala Asn Thr Asp Ile Ala Ala Phe Pro Asp Gly Lys
                405                 410                 415

ATA TAT TTT GGT GTT ACG AAA GTT GAT TTT AGT CAA TAT GAT GAT CAA       1296
Ile Tyr Phe Gly Val Thr Lys Val Asp Phe Ser Gln Tyr Asp Asp Gln
            420                 425                 430

AAA AAT GAA ACT AGT ACA CAA ACA TAT GAT TCA AAA AGA TAC AAT GGC       1344
Lys Asn Glu Thr Ser Thr Gln Thr Tyr Asp Ser Lys Arg Tyr Asn Gly
        435                 440                 445

TAT TTA GGT GCA CAG GAT TCT ATC GAC CAA TTA CCA CCA GAA ACA ACA       1392
Tyr Leu Gly Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCA GAA       1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG       1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAA ATT       1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGC GCT TCC       1584
Thr Gln Leu Pro Val Val Lys Ala Tyr Ala Leu Ser Ser Gly Ala Ser
        515                 520                 525
```

```
ATT ATT GAA GGT CCA GGA TTC ACA GGA GGA AAT TTA CTA TTC CTA AAA          1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACC TTA AAT TCA GCA          1680
Glu Ser Ser Asn Ser Ile Ala Lys Phe Lys Val Thr Leu Asn Ser Ala
545                 550                 555                 560

GCC TTG TTA CAA CGA TAT CGC GTA AGA ATA CGC TAT GCT TCA ACC ACT          1728
Ala Leu Leu Gln Arg Tyr Arg Val Arg Ile Arg Tyr Ala Ser Thr Thr
                565                 570                 575

AAC CTA CGA CTT TTC GTG CAA AAT TCA AAC AAT GAT TTT CTT GTC ATC          1776
Asn Leu Arg Leu Phe Val Gln Asn Ser Asn Asn Asp Phe Leu Val Ile
            580                 585                 590

TAC ATT AAT AAA ACT ATG AAT ATA GAT GGT GAT TTA ACA TAT CAA ACA          1824
Tyr Ile Asn Lys Thr Met Asn Ile Asp Gly Asp Leu Thr Tyr Gln Thr
        595                 600                 605

TTT GAT TTC GCA ACT AGT AAT TCT AAT ATG GGA TTC TCT GGT GAT ACA          1872
Phe Asp Phe Ala Thr Ser Asn Ser Asn Met Gly Phe Ser Gly Asp Thr
610                 615                 620

AAT GAC TTT ATA ATA GGA GCA GAA TCT TTC GTT TCT AAT GAA AAA ATC          1920
Asn Asp Phe Ile Ile Gly Ala Glu Ser Phe Val Ser Asn Glu Lys Ile
625                 630                 635                 640

TAT ATA GAT AAG ATA GAA TTT ATC CCA GTA CAA                              1953
Tyr Ile Asp Lys Ile Glu Phe Ile Pro Val Gln
                645                 650
```

(2) INFORMATION FOR SEQ ID NO:4:

(i) SEQUENCE CHARACTERISTICS:
        (A) LENGTH: 651 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Bacillus thuringiensis
        (B) STRAIN: tolworthi
        (C) INDIVIDUAL ISOLATE: 43f &nbs -continued

```
Asn Ala Ile Trp Pro Ser Asp Ala Asp Pro Trp Lys Ala Phe Met Ala
            100                 105                 110
Gln Val Glu Val Leu Ile Asp Lys Lys Ile Glu Glu Tyr Ala Lys Ser
        115                 120                 125
Lys Ala Leu Ala Glu Leu Gln Gly Leu Gln Asn Asn Phe Glu Asp Tyr
    130                 135                 140
Val Asn Ala Leu Asp Ser Trp Lys Lys Ala Pro Val Asn Leu Arg Ser
145                 150                 155                 160
Arg Arg Ser Gln Asp Arg Ile Arg Glu Leu Phe Ser Gln Ala Glu Ser
                165                 170                 175
His Phe Arg Asn Ser Met Pro Ser Phe Ala Val Ser Lys Phe Glu Val
            180                 185                 190
Leu Phe Leu Pro Thr Tyr Ala Gln Ala Ala Asn Thr His Leu Leu Leu
        195                 200                 205
Leu Lys Asp Ala Gln Val Phe Gly Glu Glu Trp Gly Tyr Ser Ser Glu
    210                 215                 220
Asp Ile Ala Glu Phe Tyr Gln Arg Gln Leu Lys Leu Thr Gln Gln Tyr
225                 230                 235                 240
Thr Asp His Cys Val Asn Trp Tyr Asn Val Gly Leu Asn Ser Leu Arg
                245                 250                 255
Gly Ser Thr Tyr Asp Ala Trp Val Lys Phe Asn Arg Phe Arg Arg Glu
            260                 265                 270
Met Thr Leu Thr Val Leu Asp Leu Ile Val Leu Phe Pro Phe Tyr Asp
        275                 280                 285
Val Arg Leu Tyr Ser Lys Gly Val Lys Thr Glu Leu Thr Arg Asp Ile
    290                 295                 300
Phe Thr Asp Pro Ile Phe Thr Leu Asn Ala Leu Gln Glu Tyr Gly Pro
305                 310                 315                 320
Thr Phe Ser Ser Ile Glu Asn Ser Ile Arg Lys Pro His Leu Phe Asp
                325                 330                 335
Tyr Leu Arg Gly Ile Glu Phe His Thr Arg Leu Arg Pro Gly Tyr Ser
            340                 345                 350
Gly Lys Asp Ser Phe Asn Tyr Trp Ser Gly Asn Tyr Val Glu Thr Arg
        355                 360                 365
Pro Ser Ile Gly Ser Asn Asp Thr Ile Thr Ser Pro Phe Tyr Gly Asp
    370                 375                 380
Lys Ser Ile Glu Pro Ile Gln Lys Leu Ser Phe Asp Gly Gln Lys Val
385                 390                 395                 400
Tyr Arg Thr Ile Ala Asn Thr Asp Ile Ala Ala Phe Pro Asp Gly Lys
                405                 410                 415
Ile Tyr Phe Gly Val Thr Lys Val Asp Phe Ser Gln Tyr Asp Asp Gln
            420                 425                 430
Lys Asn Glu Thr Ser Thr Gln Thr Tyr Asp Ser Lys Arg Tyr Asn Gly
        435                 440                 445
Tyr Leu Gly Ala Gln Asp Ser Ile Asp Gln Leu Pro Pro Glu Thr Thr
    450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
            500                 505                 510
Thr Gln Leu Pro Val Val Lys Ala Tyr Ala Leu Ser Ser Gly Ala Ser
```

-continued

```
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Ile Asp Gly Asp Leu Thr Tyr Gln Thr
        595                 600                 605

Phe Asp Phe Ala Thr Ser Asn Ser Asn Met Gly Phe Ser Gly Asp Thr
    610                 615                 620

Asn Asp Phe Ile Ile Gly Ala Glu Ser Phe Val Ser Asn Glu Lys Ile
625                 630                 635                 640

Tyr Ile Asp Lys Ile Glu Phe Ile Pro Val Gln
                645                 650
```

(2) INFORMATION FOR SEQ ID NO:5:

(i) SEQUENCE CHARACTERISTICS:
(A) LENGTH: 1425 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: BACILLUS THURINGIENSIS
(C) INDIVIDUAL ISOLATE: PS86A1

(vii) IMMEDIATE SOURCE:
(B) CLONE: E. coli NM522(pMYC2320) NRRL B-18769

(ix) FEATURE:
(A) NAME/KEY: mat_peptide
(B) LOCATION: 1..1425

(xi) SEQUENCE DESCRIPTION: SEQ ID NO:5:

```
ATGATTATTG ATAGTAAAAC GACTTTACCT AGACATTCAC TTATTCATAC AATTAAATTA     60

AATTCTAATA AGAAATATGG TCCTGGTGAT ATGACTAATG GAAATCAATT TATTATTTCA    120

AAACAAGAAT GGGCTACGAT TGGAGCATAT ATTCAGACTG GATTAGGTTT ACCAGTAAAT    180

GAACAACAAT TAAGAACACA TGTTAATTTA AGTCAGGATA TATCAATACC TAGTGATTTT    240

TCTCAATTAT ATGATGTTTA TTGTTCTGAT AAAACTTCAG CAGAATGGTG GAATAAAAAT    300

TTATATCCTT TAATTATTAA ATCTGCTAAT GATATTGCTT CATATGGTTT TAAAGTTGCT    360

GGTGATCCTT CTATTAAGAA AGATGGATAT TTTAAAAAAT TGCAAGATGA ATTAGATAAT    420

ATTGTTGATA ATAATTCCGA TGATGATGCA ATAGCTAAAG CTATTAAAGA TTTTAAAGCG    480

CGATGTGGTA TTTTAATTAA AGAAGCTAAA CAATATGAAG AAGCTGCAAA AAATATTGTA    540

ACATCTTTAG ATCAATTTTT ACATGGTGAT CAGAAAAAAT TAGAAGGTGT TATCAATATT    600

CAAAAACGTT TAAAAGAAGT TCAAACAGCT CTTAATCAAG CCCATGGGGA AAGTAGTCCA    660

GCTCATAAAG AGTTATTAGA AAAAGTAAAA AATTTAAAAA CAACATTAGA AAGGACTATT    720

AAAGCTGAAC AAGATTTAGA GAAAAAAGTA GAATATAGTT TTCTATTAGG ACCATTGTTA    780
```

-continued

```
GGATTTGTTG TTTATGAAAT TCTTGAAAAT ACTGCTGTTC AGCATATAAA AAATCAAATT    840

GATGAGATAA AGAAACAATT AGATTCTGCT CAGCATGATT TGGATAGAGA TGTTAAAATT    900

ATAGGAATGT TAAATAGTAT TAATACAGAT ATTGATAATT TATATAGTCA AGGACAAGAA    960

GCAATTAAAG TTTTCCAAAA GTTACAAGGT ATTTGGGCTA CTATTGGAGC TCAAATAGAA   1020

AATCTTAGAA CAACGTCGTT ACAAGAAGTT CAAGATTCTG ATGATGCTGA TGAGATACAA   1080

ATTGAACTTG AGGACGCTTC TGATGCTTGG TTAGTTGTGG CTCAAGAAGC TCGTGATTTT   1140

ACACTAAATG CTTATTCAAC TAATAGTAGA CAAAATTTAC CGATTAATGT TATATCAGAT   1200

TCATGTAATT GTTCAACAAC AAATATGACA TCAAATCAAT ACAGTAATCC AACAACAAAT   1260

ATGACATCAA ATCAATATAT GATTTCACAT GAATATACAA GTTTACCAAA TAATTTTATG   1320

TTATCAAGAA ATAGTAATTT AGAATATAAA TGTCCTGAAA ATAATTTTAT GATATATTGG   1380

TATAATAATT CGGATTGGTA TAATAATTCG GATTGGTATA ATAAT                  1425
```

(2) INFORMATION FOR SEQ ID NO:6:

(i) SEQUENCE CHARACTERISTICS:
        (A) LENGTH: 475 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: BACILLUS THURINGIENSIS
        (C) INDIVIDUAL ISOLATE: PS86A1

(vii) IMMEDIATE SOURCE:
        (B) CLONE: E. coli NM522(pMYC2320) NRRL B-18769

(ix) FEATURE:
        (A) NAME/KEY: Protein
        (B) LOCATION: 1..475

(xi) SEQUENCE DESCRIPTION: SEQ ID NO:6:

```
Met Ile Ile Asp Ser Lys Thr Thr Leu Pro Arg His Ser Leu Ile His
  1               5                  10                  15

Thr Ile Lys Leu Asn Ser Asn Lys Lys Tyr Gly Pro Gly Asp Met Thr
             20                  25                  30

Asn Gly Asn Gln Phe Ile Ile Ser Lys Gln Glu Trp Ala Thr Ile Gly
         35                  40                  45

Ala Tyr Ile Gln Thr Gly Leu Gly Leu Pro Val Asn Glu Gln Gln Leu
     50                  55                  60

Arg Thr His Val Asn Leu Ser Gln Asp Ile Ser Ile Pro Ser Asp Phe
 65                  70                  75                  80

Ser Gln Leu Tyr Asp Val Tyr Cys Ser Asp Lys Thr Ser Ala Glu Trp
                 85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
```

-continued

```
            145                 150                 155                 160
Arg Cys Gly Ile Leu Ile Lys Glu Ala Lys Gln Tyr Glu Glu Ala Ala
                165                 170                 175
Lys Asn Ile Val Thr Ser Leu Asp Gln Phe Leu His Gly Asp Gln Lys
            180                 185                 190
Lys Leu Glu Gly Val Ile Asn Ile Gln Lys Arg Leu Lys Glu Val Gln
            195                 200                 205
Thr Ala Leu Asn Gln Ala His Gly Glu Ser Ser Pro Ala His Lys Glu
            210                 215                 220
Leu Leu Glu Lys Val Lys Asn Leu Lys Thr Thr Leu Glu Arg Thr Ile
225                 230                 235                 240
Lys Ala Glu Gln Asp Leu Glu Lys Lys Val Glu Tyr Ser Phe Leu Leu
                245                 250                 255
Gly Pro Leu Leu Gly Phe Val Val Tyr Glu Ile Leu Glu Asn Thr Ala
            260                 265                 270
Val Gln His Ile Lys Asn Gln Ile Asp Glu Ile Lys Lys Gln Leu Asp
            275                 280                 285
Ser Ala Gln His Asp Leu Asp Arg Asp Val Lys Ile Ile Gly Met Leu
            290                 295                 300
Asn Ser Ile Asn Thr Asp Ile Asp Asn Leu Tyr Ser Gln Gly Gln Glu
305                 310                 315                 320
Ala Ile Lys Val Phe Gln Lys Leu Gln Gly Ile Trp Ala Thr Ile Gly
                325                 330                 335
Ala Gln Ile Glu Asn Leu Arg Thr Thr Ser Leu Gln Glu Val Gln Asp
            340                 345                 350
Ser Asp Asp Ala Asp Glu Ile Gln Ile Glu Leu Glu Asp Ala Ser Asp
            355                 360                 365
Ala Trp Leu Val Val Ala Gln Glu Ala Arg Asp Phe Thr Leu Asn Ala
            370                 375                 380
Tyr Ser Thr Asn Ser Arg Gln Asn Leu Pro Ile Asn Val Ile Ser Asp
385                 390                 395                 400
Ser Cys Asn Cys Ser Thr Thr Asn Met Thr Ser Asn Gln Tyr Ser Asn
                405                 410                 415
Pro Thr Thr Asn Met Thr Ser Asn Gln Tyr Met Ile Ser His Glu Tyr
            420                 425                 430
Thr Ser Leu Pro Asn Asn Phe Met Leu Ser Arg Asn Ser Asn Leu Glu
            435                 440                 445
Tyr Lys Cys Pro Glu Asn Asn Phe Met Ile Tyr Trp Tyr Asn Asn Ser
            450                 455                 460
Asp Trp Tyr Asn Asn Ser Asp Trp Tyr Asn Asn
465                 470                 475
```

(2) INFORMATION FOR SEQ ID NO:7:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

```
                              -continued (vi) ORIGINAL SOURCE:
        (A) ORGANISM: Bacillus thuringiensis
        (B) STRAIN: PS86A1

(xi) SEQUENCE DESCRIPTION: SEQ ID NO:7:

ATGATTGATT CTAAAACAAC ATTACCAAGA CATTCWTTAA TWCATACWAT WAA            53
```

PROCESS FOR CONTROLLING LEPIDOPTERON PESTS

CROSS-REFERENCE TO RELATED APPLICATIONS

This application is a continuation-in-part of U.S. application Ser. No. 07/758,020, filed Sep. 12, 1991, now U.S. Pat. No. 5,286,485 which is a continuation-in-part of U.S. application Ser. No. 07/642,112, filed Jan. 16, 1991, now U.S. Pat. No. 5,277,905 Ser. No. 07/758,020 is also a continuation-in-part of U.S. application Ser. No. 07/658,935, filed Feb. 21, 1991 now abandoned.

BACKGROUND OF THE INVENTION

The soil microbe *Bacillus thuringiensis* (B.t.) is a Gram-positive, spore-forming bacterium characterized by parasporal crystalline protein inclusions. These often appear microscopically as distinctively shaped crystals. The proteins are highly toxic to pests and specific in their activity. The toxin genes have been isolated and sequenced, and recombinant DNA-based B.t. products produced and approved. In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBTECH 6:S4–S7). Thus, isolated B.t. endotoxin genes are becoming commercially valuable.

*Bacillus thuringiensis* produces a proteinaceous paraspore or crystal which is toxic upon ingestion by a susceptible insect host. Over the past 30 years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a delta endotoxin which is toxic to the larvae of a number of lepidopteran insects.

In recent years, however, investigators have discovered B.t. pesticides with specificities for a much broader range of pests. For example, other species of B.t., namely *israelensis* and *san diego* (a.k.a. *B.t. tenebrionis,* a.k.a. M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis,*" *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe a B.t. isolate named *Bacillus thuringiensis* var. *tenebrionis,* which is reportedly active against two beetles in the order Coleoptera. These are the Colorado potato beetle, *Leptinotarsa decemlineata,* and *Agelastica alni.*

Recently, many new subspecies of B.t. have been identified, and many genes responsible for active δ-endotoxin proteins have been isolated (Höfte, H., H. R. Whiteley [1989] *Microbiological Reviews* 52(2):242–255). Höfte and Whiteley classified 42 B.t. crystal protein genes into 14 distinct genes, grouped into 4 major classes based on amino-acid sequence and host range. The classes were CryI (Lepidoptera-specific), CryII (Lepidoptera- and Diptera-specific), CryIII (Coleoptera-specific), and CryIV (Diptera-specific). The discovery of strains specifically toxic to protozoan pathogens, animal-parasitic liver flukes (Trematoda), or mites (Acari) has broadened the potential B.t. product spectrum even further. With activities against unique targets, these novel strains retain their very high biological specificity; nontarget organisms remain unaffected. The availability of a large number of diverse B.t. toxins may also enable farmers to adopt product-use strategies that minimize the risk that B.t.-resistant pests will arise.

The cloning and expression of a B.t. crystal protein gene in *Escherichia coli* has been described in the published literature (Schnepf, H. E., H. R. Whitely [1981] *Proc. NatL Acad. Sci. USA* 78:2893–2897). U.S. Pat. No. 4,448,885 and U.S. Pat. No. 4,467,036 both disclose the expression of B.t. crystal protein in *E. coli*. U.S. Pat. No. 4,853,331 discloses *B. thuringiensis* strain *san diego* (a.k.a. *B.t. tenebrionis,* a.k.a. M-7) which can be used to control coleopteran pests in various environments. U.S. Pat. No. 4,849,217 discloses *Bacillus thuringiensis* isolates active against the alfalfa weevil. One of the isolates disclosed is *B. thuringiensis* PS86A1 (NRRL B-18400).

BRIEF SUMMARY OF THE INVENTION

The subject invention concerns a novel process for controlling lepidopteran pests. This process results from the unexpected discovery that certain coleopteran-active B.t. isolates also have activity against lepidopteran pests, e.g., the diamondback moth (*Plutella xylostella*). This discovery was particularly surprising because known coleopteran-active isolates such as *Bacillus thuringiensis* var. *tenebrionis* (Krieg et al., supra) (hereinafter referred to as M-7) are not toxic to Lepidoptera.

More specifically, the subject invention process uses B.t. microbes, or variants thereof, and/or their toxins, to control lepidopteran pests. Specific B.t. microbes useful according to the invention are B.t. PS86A1, B.t. PS50C, and B.t. PS43F. Further, the subject invention also includes the use of variants of the B.t. isolates of the invention which have substantially the same lepidopteran-active properties as the specifically exemplified B.t. isolates. Procedures for making mutants are well known in the microbiological art. Ultraviolet light and nitrosoguanidine are used extensively toward this end.

The subject invention also includes the use of genes from the B.t. isolates of the invention which genes encode the lepidopteran-active toxins.

Still further, the invention also includes the treatment of substantially intact B.t. cells, and recombinant cells containing the genes of the invention, to prolong the lepidopteran activity when the substantially intact cells are applied to the environment of a target pest. Such treatment can be by chemical or physical means, or a combination of chemical and physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

Finally, the subject invention further concerns plants which have been transformed with genes encoding lepidopteran-active toxins.

BRIEF DESCRIPTION OF THE SEQUENCES

SEQ ID NO. 1 is the nucleotide sequence (open reading frame only) of the gene designated 50C.

SEQ ID NO. 2 is the predicted amino acid sequence of the toxin 50C.

SEQ ID NO. 3 is the composite nucleotide and amino acid sequences of the gene designated 43F.

SEQ ID NO. 4 is the predicted amino acid sequence of the toxin 43F.

SEQ ID NO. 5 is the nucleotide sequence (open reading frame only) of the gene designated 86A1.

SEQ ID NO. 6 is the predicted amino acid sequence of the toxin 86A1.

SEQ ID NO. 7 is an oligonucleotide probe designated 86A1-A.

DETAILED DISCLOSURE OF THE INVENTION

The *Bacillus thuringiensis* isolates useful according to the subject invention have the following characteristics in their biologically pure form:

Characteristics of B.t. PS50C

Colony morphology—Large colony, dull surface, typical B.t.

Vegetative cell morphology—typical B.t.

Culture methods—typical for B.t.

Flagellar serotyping—PS50C belongs to serotype 18, kumamotoensis.

Crystal morphology—a sphere.

RFLP analysis—Southern hybridization of total DNA distinguishes B.t. PS50C from B.t.s.d. and other B.t. isolates.

Alkali-soluble proteins—SDS polyacrylamide gel electrophoresis (SDS-PAGE) shows a 130 kDa doublet protein.

The characteristics of B.t. PS86A1 with regard to colony morphology, vegetative cell morphology and culture methods are as given above for B.t. PS50C. However, these isolates differ, as shown in Table 1, with respect to inclusions, serotype, and molecular weights of toxins.

B.t. PS43F is disclosed in U.S. Pat. No. 4,996,155.

A comparison of the characteristics of the *B. thuingiensis* strains of the subject invention to the characteristics of the known B.t. strains *B. thuingiensis* var. *tenebrionis* (M-7) and *B. thuringiensis* var. kurstaki (HD-1) is shown in Table 1.

| Culture | Accession Number | Deposit Date |
|---|---|---|
| *Bacillus thuringiensis* PS50C | NRRL B-18746 | January 9, 1991 |
| *E. coli* NM522(pMYC1638) | NRRL B-18751 | January 11, 1991 |
| *Bacillus thuringiensis* PS86A1 | NRRL B-18400 | August 16, 1988 |
| *E. coli* NM522(pMYC2320) | NRRL B-18769 | February 14, 1991 |
| *Bacillus thuringiensis* PS43F | NRRL B-18298 | February 2, 1988 |
| *E. coli* XL1-Blue (pM1,98-4) | NRRL B-18291 | January 15, 1988 |

The cultures are on deposit in the permanent collection of the Northern Research Laboratory, U.S. Department of Agriculture, Peoria, Ill., USA.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The lepidopteran toxin genes of the subject invention can be isolated by known procedures and can be be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the

TABLE 1

Comparison of B.t. PS50C, B.t. PS86A1, B.t. PS43F, B.t.t. (M-7) and B.t. HD-1

| | Bt PS50C | B.t. PS86A1 | B.t. PS43F | B.t. HD-1 | M-7 |
|---|---|---|---|---|---|
| Inclusions: | Sphere | Multiple attached | Flat, pointed, ellipse, plus small inclusions | Bipyramid | Flat square |
| Approximate molecular wt. of proteins by SDS-PAGE (kDa) | 130,000 doublet | 58,000 45,000 | 75,000 68,000 61,000 | 130,000 68,000 | 72,000 64,000 |
| Serotype | kumamotoensis | wuhenensis | tolworthi | kurstaki | morrisoni |

B.t. isolates useful according to the subject invention have been deposited. Also deposited are recombinant microbes comprising the B.t. genes of interest.

unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is important that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Ciyptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R glutinis, R marina, R aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression begins. Other techniques may employ a specific nutrient medium in the laboratory, which inhibits the expression of the toxin, where the nutrient medium in the environment allows for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon (s), a terminator region, and optionally, a polyadenylation signal.

In the direction of transcription, namely in the 5' to 3' direction of the coding or sense sequence, the construct can involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al. (1982) J. Bacteriol. 150:6069, and Bagdasarian et al. (1981) *Gene* 16:237, and U.S. Pat. Nos. 4,356,270, 4,362,817, and 4,371,625.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, and the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

The B.t. gene can be introduced between the transcriptional and translational initiation region and the transcriptional and translational termination region, so as to be under the regulatory control of the initiation region. This construct can be included in a plasmid, which could include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

The cell will usually be intact and be substantially in the proliferative form when treated, rather than in a spore form, although in some instances spores may be employed.

Treatment of the microbial cell, e.g., a microbe containing the B.t. lepidopteran toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L. [1967] *Animal Tissue Techniques*, W. H. Freeman and Company); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Eiwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cellular host containing the B.t. lepidopteran gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least about 1% by weight and may be about 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *Bacillus thuringiensis* Isolates

A subculture of a B.t. isolate of the invention can be used to inoculate the following medium, a peptone, glucose, salts medium.

| | |
|---|---|
| Bacto Peptone | 7.50 g/l |
| Glucose | 1.00 g/l |
| KH$_2$PO$_4$ | 3.40 g/l |
| K$_2$HPO$_4$ | 4.35 g/l |
| Salt Solution | 5.00 ml/l |
| CaCl$_2$ Solution | 5.00 ml/l |
| pH 7.2 | |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Cloning of a Toxin Gene from B.t. Isolate PS50C

Total cellular DNA was prepared from *Bacillus thuringiensis* (B.t.) cells grown to an optical density, at 600 nm, of 1.0. The cells were recovered by centrifugation and protoplasts were prepared in TES buffer (30 mM Tris-HCl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). Nucleic acids were precipitated with ethanol and DNA was purified by isopycnic banding on cesium chloride-ethidium bromide gradients.

Total cellular DNA from B.t. subsp. kumamotoensis (B.t. kum.), isolate PS50C, was digested with HindIII and fractionated by electrophoresis on a 0.8% (w/v) agarose-TAE (50 mM Tris-HCl, 20 mM NaOAc, 2.5 mM EDTA, pH=8.0) buffered gel. A Southern blot of the gel was hybridized with a [$^{32}$P]-radiolabeled oligonucleotide probe. Results showed that the hybridizing fragments of PS50C are approximately 12 kb and 1.7 kb in size.

A library was constructed from PS50C total cellular DNA partially digested with Sau3A and size fractionated by gel electrophoresis. The 9-23 kb region of the gel was excised and the DNA was electroeluted and then concentrated using an Elutip-d™ ion exchange column (Schleicher and Schuel, Keene, NH). The isolated Sau3A fragments were ligated into BamHI-digested LambdaGEM-11™ (PROMEGA). The packaged phage were plated on *E. coli* KW251 cells (PROMEGA) at a high titer and screened using the radiolabeled oligonucleotide probe. Hybridizing plaques were purified and rescreened at a lower plaque density. Single isolated, purified plaques that hybridized with the probe were used to infect *E. coli* KW251 cells in liquid culture for preparation of phage for DNA isolation. DNA was isolated by standard procedures. Preparative amounts of DNA were digested with XhoI (to release the inserted DNA from lambda sequences) and separated by electrophoresis on a 0.6% agarose-TAE gel. The large fragments were purified by ion exchange chromatography as above and ligated to XhoI-digested, dephosphorylated pHTBlueII (an *E. coil/B. thuringiensis* shuttle vector comprised of pBluescript s/k [Stratagene] and the replication origin from a resident B.t. plasmid [D. Lereclus et al [1989] *FEMS Microbiology Letters* 60:211–218]). The ligation mix was introduced by transformation into competent *E. coli* NM522 cells (ATCC 47000) and plated on LB agar containing ampicillin, isopropyl-(β)-D-thiogalactoside (IPTG) and 5-bromo-4-chloro-4-indolyl-(β)-D-galactoside (XGAL). White colonies, with putative restriction fragment insertions in the (β)-galactosidase gene of pHTBlueII, were subjected to standard rapid plasmid purification procedures. Plasmids were analyzed by XhoI digestion and agarose gel electrophoresis. The desired plasmid construct, pMYC1638, contains an approximately 12 kb XhoI insert. The nucleotide sequence (open reading frame only) is shown in SEQ ID NO. 1. The predicted amino acid sequence of the toxin is shown in SEQ ID NO. 2.

Plasmid pMYC1638 was introduced into an acrystalliferous (Cry$^-$) B.t. host (HD-1 cryB obtained from A. Aronson, Purdue University) by electroporation. Expression of an approximately 130 kDa protein was verified by SDS-PAGE.

Plasmid pMYC1638 containing the B.t. toxin gene, can be removed from the transformed host microbe by use of standard well-known procedures. For example, *E. coli* NM522[pMYC1638] NRRL B-18751 can be subjected to cleared lysate isopycnic density gradient procedures, and the like, to recover pMYC1638.

EXAMPLE 3

Cloning of Toxin Gene From B.t. Isolate PS43F and Transformation into Pseudomonas Total cellular DNA was prepared by growing the cells of B.t. isolate PS43F and M-7 to a low optical density (OD$_{600}$=

1.0) and recovering the cells by centrifugation. The cells were protoplasted in a buffer containing 20% sucrose and 50 mg/ml lysozyme. The protoplasts were lysed by addition of SDS to a final concentration of 4%. The cellular material was precipitated overnight at 4° C. in 100 mM neutral potassium chloride. The supernate was phenol/chloroform extracted twice and the DNA precipitated in 68% ethanol. The DNA was purified on a cesium chloride gradient. DNAs from strains 43F and M-7 (as a standard of reference) were digested with EcoRI and run out on a 0.8% agarose gel. The gel was Southern blotted and probed with the nick translated ORF XmnI to PstI fragment of the toxin encoding gene isolated from M-7 (this will be subsequently referred to as Probe). The results showed 43F to hybridize to Probe at 7.5 kb which is different than the standard.

Preparative amounts of 43F DNA were digested with EcoRI and run out on a 0.8% agarose gel. The 7.5 kb region of the preparative gel was isolated and the DNA electroeluted and concentrated using an ELUTIP™-d (Schleicher and Schuell, Keene, NH) ion exchange column. A sample was blotted and probed to verify the fragment was indeed isolated. The 7.5 kb EcoRI fragment was ligated to Lambda ZAP™ EcoRI arms. The packaged recombinant phage were plated out with E. coli strain BB4 (Stratagene Cloning Systems, La Jolla, Calif.) to give high plaque density.

The plaques were screened by standard procedures with Probe. The plaques that hybridized were purified and re-screened at a lower plaque density. The resulting phage were grown with M13 helper phage (Stratagene) and the recombinant BLUESCRIPT™ plasmid was automatically excised and packaged. The "phagemid" was re-infected in XL1-blue E. coli cells (Stratagene) as part of the automatic excision process. The infected XL1-blue cells were screened for ampicillin resistance and the resulting colonies were miniprepped to find the desired plasmid pM1,98-4. The recombinant E. coli XL1-Blue (pM1,98-4) strain is called MR381.

The plasmid pM1,98-4 contained a 7.5 kb EcoRI insert. To verify that this insert was the one of interest, a Southern blot was performed and probed. The 7.5 kb band hybridized with Probe, confirming that the fragment had been cloned. Restriction endonuclease analysis of the 7.5 kb EcoRI fragment with the enzymes HindIII, PstI, SpeI, BamHI and XbaI was done to show that a gene different from M-7 had been cloned. The enzymes which cut inside the 7.5 kb EcoRI fragment were HindIII (twice) SpeI (twice) and PstI (once). The open reading frame (ORF) of the 43F gene cut once with HindIII, twice with SpeI and did not cut with XbaI, EcoRI, or BamHI. Sequence data showed an open reading frame of 1963 bp with at best 70% sequence similarity to the toxin encoding gene of M-7.

The cloned toxin gene from PS43F can be modified for expression in P. fluorescens in the following way:

(1) A plasmid containing the Ptac-promoted cryIA(b)-like toxin gene can be made using a 3-way ligation involving the Ptac promoter and toxin gene on a BamHI-PstI fragment of about 4500 bp from pM3,130-7 (from MR420, NRRL B-18332, disclosed in U.S. Pat. No. 5,055,294), a NotI-BamHI fragment of about 5500 bp from pTJS260 (containing the tetracycline resistance genes, available from Dr. Donald Helinski, U.C. San Diego), and a NotI-PstI fragment of about 6100 bp from pTJS260 (containing the replication region). The assembled plasmid is recovered following transformation of *E. coli* and growth under tetracycline selection.

(2) A plasmid containing the Ptac-promoted 43F toxin gene can be made by ligating the toxin gene-containing FspI-SspI fragment of about 2200 bp from pM1,98-4 (from MR381(pM1,98-4), NRRL B-18291) into the SmaI site of the *E. coli* vector, pKK223-3 (Pharmacia). The Ptac-promoted 43F toxin plasmid can be recovered following transformation of E. coli, growth under ampicillin selection, and screening for plasmids with inserts in the proper orientation for expression from the tac promoter by techniques well known in the art.

(3) The Ptac-promoted 43F toxin can be assembled into, for example, the pTJS260-derived vector in a three-way ligation using the 12.6 kb DNA fragment having BamHI and filled-in NsiI ends from the plasmid resulting from step 1 above, to the BamHI-NsiI Ptac-containing fragment of about 1.2 kb and the NsiI-ScaI fragment of about 2.1 kb containing the 3' end of the 43F toxin gene and adjacent vector DNA from the plasmid resulting from step 2 above.

The resulting pTJS260-derived 43F toxin expression plasmid can be introduced into *Pseudomonas fluorescens* by electroporation.

The above cloning procedures were conducted using standard procedures unless otherwise noted.

The various methods employed in the preparation of the plasmids and transformation of host organisms are well known in the art. These procedures are described in Maniatis, T., E. F. Fritsch, J. Sambrook (1982) *Molecular Cloning: A Laboratory Manual,* Cold Spring Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Boehringer Mannheim, Indianapolis, Ind., or New England BioLabs, Beverly, Mass. The enzymes were used according to the instructions provided by the supplier.

Plasmid pM1,98-4 containing the B.t. toxin gene, can be removed from the transformed host microbe by use of standard well-known procedures. For example, *E. coli* XL1-Blue (pM1,98-4) can be subjected to cleared lysate isopycnic density gradient procedures, and the like, to recover pM1,98-4.

EXAMPLE 4

Molecular Cloning of Gene Encoding a Toxin from *Bacillus thuringiensis* Strain PS86A1

Total cellular DNA was prepared from PS86A1 cells grown to an optical density, at 600 nm, of 1.0. Cells were pelleted by centrifugation and resuspended in protoplast buffer (20 mg/ml lysozyme in 0.3 M sucrose, 25 mM Tris-Cl, pH 8.0, 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE), pH 8.0, and RNAse was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE.

Restriction fragment length polymorphism (RFLP) analyses were performed by standard hybridization of southern blots of PS86A1 DNA with a $^{32}$P-labeled oligonucleotide probe designated as 86A1-A. The sequence of the 86A1-A probe was:

5' ATG ATT GAT TCT AAA ACA ACA TTA CCA AGA CAT
TCT/I/A TTA ATT/A CAT ACT/A ATT/A AA 3(SEQ ID NO. 7)

The probe was mixed at four positions, as shown. Hybridizing bands included an approximately 3.6 kbp HindIII fragment and an approximately 9.3 kbp EcoRV fragment.

A gene library was constructed from PS86A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega, Madison, Wis.). Recombinant phage were packaged and plated on E. coli KW251 cells (Promega). Plaques were screened by hybridization with the radiolabeled 86A1-A oligonucleotide probe. Hybridizing phage were plaque-purified and used to infect liquid cultures of *E. coli* KW251 cells for isolation of phage DNA by standard procedures (Maniatis et al. [1982] *Molecular Cloning: A Laboratory Manual,* Cold Spring Harbor Laboratory, Cold Spring Harbor, N.Y.). For subcloning, preparative amounts of DNA were digested with EcoRI and SalI, and electrophoresed on an agarose gel. The approximately 2.9 kbp band containing the toxin gene was excised from the gel, electroeluted from the gel slice, and purified by ion exchange chromatography as above. The purified DNA insert was ligated into EcoRI+SalI-digested pHTBlueII (an *E. coli*/B.t. shuttle vector comprised of pBlueScript S/K, Stratagene, San Diego, Calif.) and the replication origin from a resident B.t. plasmid (D. Lereclus et al. [1989] *FEMS Microbiol. Lea.* 60:211–218). The ligation mix was used to transform frozen, competent *E. coli* NM522 cells (ATCC 47000). Transformants were plated on LB agar (Maniatis et al., supra) containing ampicillin, isopropyl-($\mu$)-D-thiogalactoside (IPTG), and 5-bromo-4-chloro-3-indolyl-($\mu$)-D-galactoside (XGAL). Plasmids were purified from putative recombinants by alkaline lysis (Maniatis et al., supra) and analyzed by electrophoresis of EcoRI and SalI digests on agarose gels. The desired plasmid construct, pMYC2320, contains the toxin gene of the invention. The DNA sequence of this gene is shown in SEQ ID NO. 5. The toxin expressed by this gene is shown in SEQ ID NO. 6.

Plasmid pMYC2320 was introduced into an acrystalliferous ($Cry^-$) B.t. host (B.t. HD-1 Cry B, A. I. Aronson, Purdue University, West Lafayatte, Ind.) by electroporation. Expression of an approximately 58 kDa protein is verified by SDS-PAGE analysis.

Plasmid pMYC2320 containing the B.t. toxin gene, can be removed from the transformed host microbe by use of standard well-known procedures. For example, *E. coli* NM522(pMYC2320) can be subjected to cleared lysate isopycnic density gradient procedures, and the like, to recover pMYC2320.

EXAMPLE5

43F Toxin Production by a Transformed *Pseudomonas fluorescens* Host

A transformed *Pseudomonas fluorescens* containing the PS43F gene was grown in the following medium using a 1% inoculum grown in LB medium with 30 $\mu$g/ml tetracycline:

| | |
|---|---|
| Glycerol | 65 g/L |
| Na citrate.$2H_2O$ | 7.14 |
| HCT | 20 |
| Amberex 1003 | 20 |
| $NaNO_3$ | 5 |
| $(NH_4)_2SO_4$ | 2.3 |

32° C. at 300 rpm.

These were 72 hour fermentations with induction and supplementation taking place at 24 hours. They were induced with 2 mM IPTG and supplemented with the following:

| | |
|---|---|
| Amisoy | 20.0 g/L |
| $MgSO_4.7H_2O$ | 0.4 |
| $K_2HPO_4$ | 1.6 |
| KCl | 1.6 |

The toxin concentration can be determined using laser densitometry (LKB) to quantify the approximately 70 kDa toxin protein found in the *P. fluorescens* host after Coomassie staining of polyacrylamide gels containing SDS.

EXAMPLE 6

Testing of B.t. Toxins Against the Diamondback Moth (A) A spore crystal preparation of a B.t. clone comprising the PS86A1 gene was toxic to the lepidopteran pest, diamondback moth *Plutella xylostella,* in a 1.5% agar artificial diet assay. The B.t. clone was grown as disclosed in Example 1. Rates greater than 100 microgram protein/gram diet gave 100% control of this pest in 6 days.

(B) A spore crystal preparation of a B.t. clone comprising the PS50C gene was toxic to the lepidopteran pest, diamondback moth, in a 1.5% agar artificial diet assay. The B.t. clone was grown as disclosed in Example 1. Rates greater than 100 microgram protein/gram diet gave 100% control of this pest in 6 days.

(C) A *Pseudomonas fluorescens* clone comprising the PS43F gene was toxic to the lepidopteran pest, diamondback moth, in a 1.5% agar artificial diet assay. Rates greater than 40 microgram protein/gram diet gave 100% control of this pest in 6 days.

EXAMPLE 7

Further Testing of B.t.Toxins Against the Diamondback Moth

Toxins of the subject invention were produced by recombinant cells which had been transformed with genes according to the subject invention. The toxins produced by the recombinant cells were then tested for their activity against diamondback moths. The results of these experiments are shown in Table 2. These experiments were conducted as described in Example 6.

TABLE 2

| Source strain | Cloned Toxin Gene | Host | Clone | Diamondback Moth $LC_{50}$ (µg toxin/g diet) |
|---|---|---|---|---|
| PS86A1 | 86A1 | B. thuringiensis | MR506 | 79 |
| PS50C | 50C | B. thuringiensis | MR505 | 19 |
| PS43F | 43F | P. fluorescens | MR816 | 11 |

EXAMPLE 8

Insertion of Toxin Genes Into Plants

One aspect of the subject invention is the transformation of plants with genes encoding a lepidopteran toxin. The transformed plants are resistant to attack by lepidopterans.

Genes encoding lepidopteran-active toxins, as disclosed herein, can be inserted into plant cells using a variety of techniques which are well known in the art. For example, a large number of cloning vectors comprising a replication system in E. coli and a marker that permits selection of the transformed cells are available for preparation for the insertion of foreign genes into higher plants. The vectors comprise, for example, pBR322, pUC series, M13mp series, pACYC184, etc. Accordingly, the sequence encoding the B.t. toxin can be inserted into the vector at a suitable restriction site. The resulting plasmid is used for transformation into E. coli. The E. coli cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al, *Crit. Rev. Plant Sci.* 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in E. coli and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 9

Cloning of Novel B.t. Genes Into Insect Viruses

A number of viruses are known to infect insects. These viruses include, for example, baculoviruses and entomopoxviruses. In one embodiment of the subject invention, lepidopteran-active genes, as described herein, can be placed with the genome of the insect virus, thus enhancing the pathogenicity of the virus. Methods for constructing insect viruses which comprise B.t. toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for controlling lepidopteran insect pests which comprises contacting said insect pests with an insect-controlling effective amount of a *Bacillus thuringiensis* isolate selected from the group consisting of B.t. PS43F, B.t. PS50C and B.t. PS86A1, and variants thereof.

2. The method, according to claim 1, wherein said *Bacillus thuringiensis* is B.t. PS43F.

3. The method, according to claim 1, wherein said *Bacillus thuringiensis* is B.t. PS50C.

4. The method, according to claim 1, wherein said *Bacillus thuringiensis* is B.t. PS86A1.

5. The method, according to claim 1, wherein said insect pest is the diamondback moth (*Plutella xylostella*).

6. The method, according to claim 1, which comprises applying an insecticidal composition comprising *Bacillus thuringiensis* to plants or soil.

7. The method, according to claim 6, wherein said insecticidal composition is a liquid.

8. The method, according to claim 6, wherein said insecticidal composition is in granular form.

9. The method, according to claim 6, wherein said insecticidal composition is applied when corn or soybean seed is planted.

10. The method, according to claim 1, wherein said *Bacillus thuringiensis* are treated to prolong their pesticidal activity in the environment of a target pest.

11. A method for controlling lepidopteran pests which comprises exposing said pests to a plant transformed by a gene obtainable from a *Bacillus thuringiensis* isolate selected from the group consisting of B.t. PS43F, B.t. PS50C and B.t. PS86A1, and variants thereof, wherein said gene encodes a toxin active against lepidopteran pests.

12. The method, according to claim 11, wherein said gene comprises the DNA of SEQ ID NO. 1 or a portion thereof which encodes a lepidopteran-active toxin.

13. The method, according to claim 11, wherein said gene comprises the DNA of SEQ ID NO. 3 or a portion thereof which encodes a lepidopteran-active toxin.

14. The method, according to claim 11, wherein said gene comprises the DNA of SEQ ID NO. 5 or a portion thereof which encodes a lepidopteran-active toxin.

15. A method for controlling lepidopteran insects which comprises administering to said insects or to the environment of said insects a microorganism transformed to express a *Bacillus thuringiensis* toxin active against lepidopteran pests encoded by DNA selected from the group consisting of SEQ ID NO. 1, SEQ ID NO. 3. SEQ ID NO. 5, and any fragments of those sequences sufficient to encode a lepidopteran-active toxin.

16. The method, according to claim 15, wherein said toxin is encoded by DNA of SEQ ID NO. 1.

17. The method, according to claim 15, wherein said toxin is encoded by DNA of SEQ ID NO. 3.

18. The method, according to claim 15, wherein said toxin is encoded by DNA of SEQ ID NO. 5.

19. The method, according to claim 15, wherein said microorganism is a Pseudomonas.

20. The method, according to claim 15, wherein said transformed microorganism is treated to prolong its pesticidal activity in the environment of a target pest.

* * * * *

UNITED STATES PATENT AND TRADEMARK OFFICE
CERTIFICATE OF CORRECTION

PATENT NO. : 6,294,184 B1
DATED : September 25, 2001
INVENTOR(S) : Kendrick Akira Uyeda and Gregory Alan Bradfisch It is certified that error appears in the above-identified patent and that said Letters Patent is hereby corrected as shown below:

Column 3,
Lines 45 and 47, "*thuingiensis*" should read -- *thuringiensis* --.

Column 5,
Line 26, "Ciyptococcus" should read -- Cryptococcus --; and
Line 34, "*R glutinis, R marina, R aurantiaca*" should read -- R. glutinis, R. marina, R. aurantiaca --.

Column 8,
Line 40, "Eiwinia" should read -- *Erwinia* --.

Column 9,
Line 40, "$CaCl_2.2H_2O$" should read -- $CaCl_2 \cdot 2H_2O$ --.

Column 10,
Line 34, "et al" should read -- *et al.* --.

Column 13,
Line 7, "TCTI/A" should read -- TCT/A --;
Line 37, "*Lea.*" should read -- *Lett.* --;
Lines 40 and 42, "($\mu$)" should read -- ($\beta$) --.

Column 15,
Line 47, "et al," should read -- *et al.,* --; and
Line 47, "et al." should read -- *et al.* --.

UNITED STATES PATENT AND TRADEMARK OFFICE
CERTIFICATE OF CORRECTION

PATENT NO. : 6,294,184 B1
DATED : September 25, 2001
INVENTOR(S) : Kendrick Akira Uyeda and Gregory Alan Bradfisch It is certified that error appears in the above-identified patent and that said Letters Patent is hereby corrected as shown below:

<u>Column 16,</u>
Line 60, *"Microbiol"* should read -- *Microbiol.* --.

Signed and Sealed this

Ninth Day of April, 2002

Attest:

JAMES E. ROGAN
*Attesting Officer*    *Director of the United States Patent and Trademark Office*